| United States Patent [19] | [11] | 4,136,178 |
|---|---|---|
| Lin et al. | [45] | Jan. 23, 1979 |

[54] LOCUST BEAN GUM THERAPEUTIC COMPOSITIONS

[75] Inventors: Song-Ling Lin; Maturu K. Pramoda, both of Rouses Point, N.Y.

[73] Assignee: American Home Products Corp., New York, N.Y.

[21] Appl. No.: 764,320

[22] Filed: Jan. 31, 1977

[51] Int. Cl.² .................... A61K 31/27; A61K 31/47; A61K 31/66; A61K 31/415

[52] U.S. Cl. .................... 424/211; 424/258; 424/273 R; 424/300; 424/361

[58] Field of Search ............. 424/361, 211, 258, 273, 424/300

[56] References Cited

U.S. PATENT DOCUMENTS

| 2,703,777 | 3/1955 | Feinstein et al. | 424/361 |
|---|---|---|---|
| 3,416,530 | 12/1968 | Ness | 424/7 |
| 3,640,741 | 2/1972 | Etes | 106/170 |
| 3,659,026 | 4/1972 | Schuppner | 424/361 |
| 3,700,451 | 10/1972 | Sullivan | 96/66 |
| 3,870,791 | 3/1975 | Haddad et al. | 424/361 |
| 3,900,569 | 8/1975 | Monti | 424/361 |
| 3,944,427 | 3/1976 | Sullivan | 106/208 |
| 4,012,333 | 3/1977 | Towle | 424/361 |

FOREIGN PATENT DOCUMENTS 2051369 6/1971 Fed. Rep. of Germany.

OTHER PUBLICATIONS

"The Pharmacopeia of the U.S.A.", 18th Revision, 9/1/70, pp. 220–221 and 505–506.

J. of Pharm. Sci., 63(5), 721–724 (1974) Lee et al., "Corneal Absorption of Ophthalmic Drugs".

*Primary Examiner*—Albert T. Meyers
*Assistant Examiner*—D. W. Robinson
*Attorney, Agent, or Firm*—Adley F. Mandel

[57] ABSTRACT

Ophthalmic compositions are disclosed comprising an ophthalmic drug and locust bean gum.

12 Claims, No Drawings

LOCUST BEAN GUM THERAPEUTIC COMPOSITIONS

BACKGROUND OF THE INVENTION

1. Field of the Invention

This invention relates to the use of gums as adjuvants in ophthalmic compositions to potentiate the miotic response to cholinergic agents, particularly echothiophate iodide which is used in treatment of glaucoma; this allows the administration of lower, more effective dosages of said cholinergic agents, thereby alleviating side effects. In a further aspect, this invention relates to a drug delivery system which is a gel and is useful for topical application.

In this application the term "adjuvant" is defined as found in *Stedman Medical Dictionary, 22nd Edition* as "that which aids or assists; denoting a remedy that is added to a prescription to assist or increase the action of the main ingredient".

2. Description of the Prior Art

The prior art discloses a variety of gums and polymers used as adjuvants in ophthalmic compositions.

For example, C. Rosenblum et. al. in Arch Ophthal, 77:234-237, 1967, disclosed the use of hydroxyethyl cellulose to increase the systemic absorption by ocular tissues of dexamethasone. With drugs such as erythromycin propionate and sulfapyridazine sodium, Y. F. Maichuk, Am. J. Ophthal, 74:694, 1972 taught the use of polyvinyl alcohol to potentiate their pharmacological response. Similarly, guar gum was found to increase the corneal absorption of tropicamide as reported by Lee et al, J. Pharm. Sci. 63:721, 1974.

The use of gum and polymer combinations is also disclosed, such as their application as a bactericidal cleanser, lubricant, and wetting agent. German Pat. No. 2,051,369 is illustrative, wherein is disclosed a solution containing polyethylene glycol, poly(ethyleneoxide), and an ophthalmic medicine. British Pat. No. 1,337,105 teaches a different combination of polymers for use in eye wash solution containing hydroxyethyl cellulose and polyvinyl alcohol. Still another example is presented by British Pat. No 1,340,518 which discloses ophthalmic compositions containing an ophthalmic medicament, a polyalkylene glycol, a cellulosic derivative or mixture of such derivatives, and, optionally, polyvinyl pyrrolidone. See also U.S. Pat. Nos. 3,944,427 and 3,700,451 which disclose gelable and gelled compositions containing agar, xanthan gum, and locust bean gum in a liquid medium for use as a carrier of therapeutic solutions, but particularly as a carrier for photoprocessing solutions. These compositions, however, are rigid gels at room temperature.

SUMMARY OF THE INVENTION

In accordance with the present invention, locust bean gum is incorporated in ophthalmic compositions of cholinergic agents, particularly echothiophate iodide, to enhance the drug's therapuetic activity thereby allowing a reduction in dosage and a concomitant reduction in toxicity while retaining an effective level of antiglaucoma activity.

The locust bean gum, included in ophthalmic solutions of echothiophate iodide, acts as an adjuvant and thus promotes the activity of the drug. The locust bean gum adjuvant is prepared by dissolving the gum in the solution vehicle followed by dissolution of the echothiophate iodide.

DETAILED DESCRIPTION OF THE INVENTION

Echothiophate iodide is described in U.S. Pat. No. 2,911,430 granted Nov. 3, 1959 to H. M. Fitch and the disclosure of that patent is incorporated herein by reference.

Locust bean gum is a high molecular weight polysaccharide derived from *Ceratonia siliqua*. Chemically, locust bean gum is a galactomannan best illustrated with galactose units located on every fourth mannose unit, with smaller amounts of pentoglycan, protein, cellulose and ash. A detailed description of the composition, physical and chemical properties, preparation, etc. of locust bean gum is given in Industrial Gums (Polysaccharides and Their Derivatives), Academic Press, (1959) at pp. 361-376, incorporated herein by reference.

In the compositions of this invention, the concentration of locust bean gum is from about 0.01% to about 2.5% weight by volume. It will be appreciated that as the concentration of the gum is increased, it is accompanied by an increase in viscosity. Thus, at concentrations of gum above, about 1.0% to about 2.5%, a gel like consistency is attained. This gel composition permits various topical applications of drug such that the drug is maintained at the site of administration over a longer period than is possible by a liquid composition. By a gel is meant a colloid in which the disperse phase has combined with the continuous phase to produce a semi-solid such as a jelly.

The preferred concentration of locust bean gum for dropwise ophthalmic applications is from about 0.02% to about 1.0% weight/volume. When echothiophate iodide, a drug used in the treatment of glaucoma, is the ophthalmic drug incorporated in said gum composition, its concentration can vary from about 0.005% to about 0.25% weight/volume. An advantage of this invention is that the systemic side effects observed at higher concentrations of echothiophate iodide may be reduced due to the potentiation of the drug's pharmacological resonse by locust bean gum thereby permitting the administration of reduced concentrations of drug. Illustratively, it was observed that a composition containing 0.03% echothiophate iodide and 0.2% locust bean gum potentiated a greater pharmacological response than one containing 0.25% echothiophate iodide and no gum.

Potentiation of pharmacologic response was observed to increase with increasing concentrations of locust bean gum. Also, required or preferred concentrations of gum needed to achieve optimum results will vary from drug to drug. Thus, while with echothiophate iodide a concentration of locust bean gum from about 0.02% to about 1.0% is preferred; with the aldose reductase inhibitor 1,3-dioxo-1 H-benz[de] isoquinoline-2(3H)-acetic acid a concentration of locust bean gum from about 0.5% to about 1.5% is preferred. The locust bean gum composition has also been found suitable as a vehicle for widely varied concentrations of drug. For example, these compositions have been found suitable for delivering as little as 0.005% weight/volume of echothiophate iodide or as much as 12.0% of Alrestatin. The choice is usually limited only by the need to incorporate therapeutically effective dosage of drug within the compositions of this invention.

An advantage of the herein disclosed invention is its superiority as an adjuvant over such previously art known adjuvants as polyvinyl alcohol, hydroxethyl cellulose, and ethylene oxide polymer as demonstrated in tests conducted with echothiophate iodide. Also, while the compositons of this invention may be prepared in an aqueous solvent, these compositons are also feasible in liquid vehicles containing water and water miscible solvents; thus, it will be appreciated that these compositions are equally well adapted to the delivery of drugs with varying degrees of solubility. By way of illustration, these compositions are stable in the presence of such non-aqueous solvents as ethanol up to 6% volume/volume, propylene glycol up to 25% volume/volume, and the like when such solvents are incorporated within the carrier system, i.e., the pharmaceutically acceptable liquid vehicle comprises 75-100% water.

The compositions of this invention can be designed by first selecting the drug to be used and the pharmacological response desired. A composition can then be designed to produce that pharmacological response comprising the locust bean gum adjuvant and the selected drug in a pharmaceutically acceptable liquid vehicle.

Any of the drugs used to treat the eye and surrounding tissues can be incorporated in the ophthalmic compositions of this invention.

Although the use of the locust bean gum adjuvant has principally been described with respect to drug delivery systems for the administration of ophthalmic drugs, it will be appreciated that the gum may be employed as well in a wide variety of bioerodable compositions for administering drugs to the other areas of the body. Thus, the pharmacuetical delivery systems of this invention may be employed to advantage in external and internal erodable drug delivery compositions such as, for example, topical, oral, nasal and buccal preparations. In each instance, the composition employs locust bean gum in combination with the selected drug and is of a shape or form appropriate for implantation or insertion in the described body tissues or cavities respectively or for application to a particular body area.

Suitable drugs for use in therapy with the compositions of the invention include antibacterials, such as, bacitracin, chloramphenicol, gentamycin, gramicidin, polymyxin, sulfacetamide, sulfisoxazole, and tetracycline; antiglaucomatous agents, such as, acetazolamide, epinephrine, and echothiophate iodide; sympathomimetic agents, such as, epinephrine, phenylephrine, cocaine, and ephedrine; parasympatholyties, such as, atropine, homatropine, scopolamine, tropicamide and cyclopentolate; parasympathomimetics, such as, carbachol, echothiophate, pilocarpine, and isofluorophate; sympatholyties, such as, dibenamine and tolazoline; anti-inflammatory agents, such as, cortisone, hydrocortisone, predinisolone, prednisone, and dexamethasone; and others, such as, antipyrine, antazoline, LH-RH, LH-FSH, and 1,3-dioxo-1H-benz[de] isoquinoline-2(3H)-acetic acid.

The term "drug" as used herein is intended to be interpreted in its broadest sense as including any composition or substance that will produce a pharmacologic response, either at the site of application or at a site remote therefrom.

Additionally, the compositions of the invention may include a variety of additives including preservatives, buffers, electrolytes, antioxidants, stabilizers, and pharmaceutically acceptable liquid vehicles as described earlier.

The invention may be illustrated in part through the following examples.

EXAMPLE 1

| Ingredients | A | B | C |
|---|---|---|---|
| Echothiophate Iodide | 0.3g | 0.3 | 2.5g |
| Locust Bean Gum | — | 2.0g | — |
| Boric Acid, Reagent Grade | 0.60 | — | 0.60g |
| Sodium Phosphate, Dried | 0.26g | — | 0.26g |
| Mannitol | 12.0g | — | 12.0g |
| Chlorobutanol, Anhydrous | 5.0g | — | 5.0g |
| Potassium Acetate | 8.0g | — | 8.0g |
| Phenylethyl Alcohol | — | 5.0ml | — |
| Hydrochloric Acid, 1N q.s. to pH 3 | — | √ | — |
| Distilled Water q.s. to | 1L | 1L | 1L |

Formulations A-C were prepared by dissolving sodium phosphate, boric acid, mannitol, chlorbutanol or phenylethyl alcohol in distilled water; dispersing the gum in the solution; autoclaving the solution at 121° C. for 60 minutes; adjusting the solutions pH where noted and filtering. Then, dissolve echothiophate iodide to prepare the test solution.

Rabbits' eyes were treated with 2 drops of the test solution of Example 1 and pupillary diameters were measured with a cathetometer. The miotic response intensity was computed by taking the difference in pupillary diameters at zero time and time "T" (i.e., hours after installation) and dividing it by the pupillary diameter at zero time. The table below illustrate the average miotic response for all eyes as a function of hours after installation.

| | AMI* AT HOURS AFTER INSTILLATION | | | | | |
|---|---|---|---|---|---|---|
| | 1 | 2 | 3 | 7 | 24 | 25 |
| A | 0.02 | 0.02 | 0.06 | 0.04 | 0.14 | 0.19 |
| B | 0.44 | 0.53 | 0.57 | 0.39 | 0.28 | 0.26 |
| C | 0.19 | 0.39 | 0.34 | 0.24 | 0.19 | 0.19 |

By comparing formulation B with formulations A and C, it is clear that the composition having the gum potentiates a significantly higher miotic response intensity than those formulations not having locust bean gum. Thus, it was observed that the dosage level of gum containing formulations can be reduced. It was also observed that the gum containing formulations could be used to deliver a sustained and controlled dosage regimen of echothiophate iodide over a 24 hour period.

EXAMPLE 2

| Ingredients | D | E | F | G | H | I |
|---|---|---|---|---|---|---|
| Echothiophate Iodide | 0.10g | 0.10g | 0.10g | 0.030g | 0.30g | 0.30g |
| Locust Bean Gum | — | 2.0g | 5.0g | — | 3.0g | 5.0g |
| Boric Acid, Reagent Grade | 0.60g | — | — | 0.60g | 0.60g | 0.60g |
| Sodium Phosphate, Dried | 0.26g | — | — | 0.26g | 0.26g | 0.26g |
| Mannitol | 12.0g | — | — | 12.0g | 12.0g | 12.0g |
| Chlorobutanol Anhydrous | 5.0g | — | — | 5.0g | 5.0g | 5.0g |
| Potassium Acetate | 2.80g | — | — | 8.0g | — | — |
| Phenylethyl Alcohol | — | 5.0ml | 5.0ml | — | — | — |
| Hydrochloric Acid, 1N | — | √ | √ | — | √ | √ |

| Ingredients | D | E | F | G | H | I |
|---|---|---|---|---|---|---|
| q.s. to pH 3 | | | | | | |
| Distilled Water q.s. to | 1L | 1L | 1L | 1L | 1L | 1L |

Formulations D–G were prepared and evaluated as in Example 1. The table below illustrates the average miotic response intensity for all eyes as a function of hours after installation.

| | AMI HOURS AFTER INSTILLATION | | | | | |
|---|---|---|---|---|---|---|
| | 1 | 2 | 3 | 7 | 24 | 25 |
| D | 0.03 | 0.09 | 0.04 | 0.02 | 0.08 | 0.08 |
| E | 0.19 | 0.33 | 0.37 | 0.32 | 0.17 | 0.16 |
| F | 0.50 | 0.64 | 0.58 | 0.32 | 0.16 | 0.05 |
| G | 0.01 | 0.02 | 0.06 | 0.05 | 0.13 | 0.18 |
| H | 0.08 | 0.18 | 0.25 | 0.28 | 0.17 | 0.13 |
| I | 0.47 | 0.68 | 0.73 | 0.54 | 0.30 | 0.32 |

The tests on formulations D–F were done simultaneously but separately from the tests on formulations G–I which were also run simultaneously. These results indicate, as in Example 1, that locust bean gum containing formulations potentiate significantly higher miotic response intentions than those formulations not having the gum adjuvant. It was observed that as the concentration of gum adjuvant increases, the degree of potentiation also increases. Thus, it was observed that lower concentrations of drug may be administered and that a sustained and controlled dosage of echothiophate iodide over a 24 hour period is feasible with the use of the gum containing formulation.

EXAMPLE 3

The following formulations containing pilocarpine hydrochloride were prepared as in Example 1.

| Ingredients | J | K |
|---|---|---|
| Pilocarpine Hydrochloride | 0.01g | 0.01g |
| Locust Bean Gum | — | 0.5g |
| Boric Acid | 1.24g | 1.24g |
| Potassium Chloride | 0.04g | 0.04g |
| Phenylethyl Alcohol | — | 0.50ml |
| Sodium Carbonate 2.12% solution in water, or 0.1NHCl, q.s. to pH 5.3 | √ | √ |
| Distilled Water q.s. to | 100ml | 100ml |

Rabbits' eyes were treated and tested as in Example 1, the results listed in the following table.

| | AMI AT HOURS AFTER INSTILLATION | | | | |
|---|---|---|---|---|---|
| Hours | 0.3 | 1 | 1.5 | 1.7 | 2 |
| K | — | 0.01 | 0.02 | 0.04 | 0.03 |
| J | 0.01 | — | −0.01 | −0.01 | −0.01 |

These results indicate that locust bean gum potentiates the miotic response intensity of pilocarpine hydrochloride.

EXAMPLE 4

Formulations containing the aldose reductase inhibitor, 1,3-dioxo-1H-benz[de]-isoquinoline-2(3H)-acetic acid, Alrestatin ® were prepared as in Example 1:

| | L | M |
|---|---|---|
| Alrestatin | 12.0g | 12.0g |
| Potassium Hydroxide | 3.25g | 3.30g |
| Xanthan Gum | — | 1.0g |
| Benzalkonium Chloride at 17% | 0.06ml | 0.06ml |
| EDTA acid | 0.10g | 0.10g |
| Potassium Hydroxide q.s. to pH 6 | √ | √ |
| Phenylethyl Alcohol | — | 1.0ml |
| Distilled Water q.s. to | 100ml | 100ml |

Potentiation of the aldose reductase inhibitor was demonstrated by measuring its ocular penetration following instillation in the eyes of unanesthesized rabbits, see below:

| OCULAR PENETRATION OF ALRESTATIN | | L | M |
|---|---|---|---|
| Aqueous Humor | (mcg/ml) | 8.5 | 10.8 |
| Cornea | (mcg/ml) | 78 | 142 |
| Lens | (mcg/ml) | 0.5 | 0.4 |

These results illustrate increase ocular penetration in formulations containing locust bean gum in combination with aldose reductase inhibitor.

EXAMPLE 5

A formulation containing the polypeptide, gonadorelin also known as luteinizing hormone-releasing hormone was prepared as in example 1 for intranasal or intramuscular application.

| LH-RH | 1.0 | g |
|---|---|---|
| Locust Bean Gum | 0.5 | g |
| Phenylethyl Alcohol | 0.5 | ml |
| Distilled Water q.s. to | 100 | ml |

The stability of this LH-RH formulation was evaluated over a one year period and found to be satisfactory.

EXAMPLE 6

Manufactured as described in example 1, formulations containing carbachol, 2-[(Aminocarbonyl)oxy]-N,N,N-trimethylethanaminium chloride were prepared.

| Formula per 50 ml | N | | O | |
|---|---|---|---|---|
| Carbachol | 0.50 | g | 1.50 | g |
| Locust Bean Gum | 0.25 | g | 0.25 | g |
| Phenylethyl Alcohol | 0.125 | ml | 0.125 | ml |
| Distilled Water q.s. to | 50 | ml | 50 | ml |

The stability of carbachol containing formulations was evaluated and found to be satisfactory.

We claim:

1. A composition consisting essentially of a therapeutically effective amount of a topically effective ophthalmic drug and about 0.01% to about 2.5% of locust bean gum in a pharmaceutically acceptable liquid vehicle, said liquid vehicle comprising about 75–100% water by volume.

2. The composition of claim 1 wherein the concentration of said locust bean gum is from about 0.02% to about 1.0%, said percentages expressed as weight per volume.

3. The composition of claim 1 wherein said ophthalmic drug is echothiophate iodide.

4. The ophthalmic composition of claim 3 wherein the concentration of said echothiophate iodide is about 0.03% to about 0.25% and wherein the concentration of said locust bean gum is from about 0.1% to about 0.5%.

5. The composition of claim 1 wherein said ophthalmic drug is pilocarpine hydrochloride.

6. The composition of claim 1 wherein said ophthalmic drug is carbachol.

7. An ophthalmic composition effective in the treatment of glaucoma consisting essentially of about 0.005% to about 0.25% echothiophate iodide and about 0.02% to about 1% of locust bean gum in a pharmaceutically acceptable liquid vehicle; said percentages expressed as weight per volume, and said liquid vehicle comprising about 75-100% water by volume.

8. An ophthalmic composition essentially of about 0.01% to about 0.05% pilocarpine hydrochloride and about 0.02% to about 1.0% locust bean gum in a pharmaceutically acceptable liquid vehicle, said liquid vehicle comprising about 75-100% water by volume.

9. An ophthalmic composition consisting essentially of a therapeutically amount of 1,3-dioxo-1H-benz[de]isoquinoline-2(3H)-acetic acid and about 0.5% to about 1.5% of locust bean gum in a pharmaceutically acceptable liquid vehicle and wherein said percentages are expressed as weight per volume, said liquid vehicle comprising about 75-100% water by volume.

10. A method for treating the eye of a mammalian patient by potentiating the pharmacological response of topically effective drugs which consists essentially of applying to said eye a liquid composition containing a therapeutically effective amount of said drug and about 0.01% to about 2.5% locust bean gum.

11. An ophthalmic gel composition for topical application consisting essentially of about 1.0% to about 2.5% of locust bean gum and a therapeutically effective amount of a topically effective ophthamic drug in a pharmaceutically acceptable liquid vehicle; said percentages expressed as weight per colume, and said liquid vehicle comprising about 75-100% water by volume.

12. An ophthalmic composition consisting essentially of about 0.2% to about 1.0% of locust bean gum and a therapeutically effective amount of carbachol in a pharmaceutically acceptable liquid vehicle, said liquid vehicle comprising about 75-100% water by volume.

* * * * *